(12) United States Patent
Hogan

(10) Patent No.: US 8,888,284 B2
(45) Date of Patent: Nov. 18, 2014

(54) FIELD OF LIGHT BASED DEVICE

(71) Applicant: Joshua Noel Hogan, Los Altos, CA (US)

(72) Inventor: Joshua Noel Hogan, Los Altos, CA (US)

( * ) Notice: Subject to any disclaimer, the term of this patent is extended or adjusted under 35 U.S.C. 154(b) by 199 days.

(21) Appl. No.: 13/668,261

(22) Filed: Nov. 3, 2012

(65) Prior Publication Data

US 2014/0002794 A1 Jan. 2, 2014

Related U.S. Application Data

(60) Provisional application No. 61/628,709, filed on Nov. 4, 2011, provisional application No. 61/667,417, filed on Jul. 3, 2012.

(51) Int. Cl.
*A61B 3/14* (2006.01)
*A61B 3/10* (2006.01)
*A61B 3/00* (2006.01)

(52) U.S. Cl.
USPC .............................. 351/206; 351/221; 351/246

(58) Field of Classification Search
USPC .......................................... 351/206, 221, 246
See application file for complete search history.

*Primary Examiner* — Jack Dinh

(57) ABSTRACT

The invention teaches a field of light based method and system suitable for non-invasive target analysis, including in vivo analysis. A embodiment of the system comprises a field of light imaging device; an illuminating module consisting of a plurality of light sources that emit light radiation centered on multiple wavelengths; a partially reflective minor positioned to reflect radiation to the target from the illumination module, and from the target to the field of light imaging device; a display; a processing and control module coordinating target position, and the synchronous output of the illumination module with image capture by the field of light imaging device; and an output and storage device.

6 Claims, 2 Drawing Sheets

FIELD OF LIGHT BASED DEVICE

CROSS REFERENCES TO RELATED APPLICATIONS

This patent application, with claims priority from provisional application No. 61/628,709, filed on Nov. 4, 2011, titled Eye Monitoring Device and System, the contents of which is incorporated by reference as if fully set forth herein. This patent application also claims priority from provisional patent application No. 61/667,417 filed on 3 Jul. 2012 titled "Improved Correlation of Concurrent Non-invasively Acquired Signals", the contents of which is incorporated by reference as if fully set forth herein.

This patent application is also related to U.S. Pat. No. 7,526,329 titled Multiple reference non-invasive analysis system and U.S. Pat. No. 7,751,862 titled Frequency resolved imaging system, the contents of both of which are incorporated by reference herein as if fully set forth. This patent application is also related to U.S. Pat. No. 7,248,907 filed on Oct. 19, 2005 titled "Correlation of Concurrent Non-invasively Acquired Signals", the contents of which is incorporated by reference as if fully set forth herein.

FIELD OF USE

The invention described and illustrated in this application relates to non-invasive analysis in general and in particular to optical non-invasive analysis of targets containing optical elements.

BACKGROUND OF THE INVENTION

Non-invasive analysis, which for purposes of this application includes non-destructive analysis, is a valuable technique for acquiring information about systems or targets without undesirable side effects, such as damaging the system being analyzed. Non-invasive analysis has a broad range of applications including, non-destructive analysis of artifacts for defects, verification of the authenticity of documents, such as, bank notes, bio-metric analysis and bio-medical analysis of living entities. In the case of analyzing living entities, such as human tissue, and in particular the human eye, undesirable side effects of invasive analysis include the risk of infection along with pain and discomfort associated with the invasive process.

It is frequently useful to make biometric measurements on the human eye, such as lens curvature, lens thickness and axial length. Such measurements are useful, for example, in choosing an appropriate artificial inter-ocular lens to replace an existing natural lens that has been degraded by cataracts. It is also valuable to make routing visual evaluation of aspects of the eye, such as the retina.

A conventional approach is to use ultrasound or an Optical Coherence Tomography (OCT) based system to measure some parameters, such as axial length and a conventional camera to assist in alignment. However, ultrasound measurements require application of a liquid to the eye for index matching and are therefore somewhat invasive, OCT systems can be costly and require depth alignment with two surfaces either simultaneously or at high speed, and a conventional camera requires focusing.

Furthermore, where images and measurements are to be taken without the aid of a skilled operator, complex focusing and alignment procedures may not be practical. For example, home or mobile use of a monitor by an untrained subject (who may have less than perfect vision) would preclude any elaborate focusing and alignment procedures.

Digital Light Field Photography is well known. Recent developments in computer science and fabrication techniques of detector and micro-lens arrays make Digital Light Field Photography technical feasible for consumer devices. A good treatment of Digital Light Field Photography may be found in the dissertation of Ren Ng, entitled "Digital Light Field Photography", copyright 2006 submitted to Stanford University in partial fulfillment of the requirements for the degree of doctor of philosophy.

Digital Light Field Photography does not require a skilled operator for focusing. Moreover Digital Light Field Photography provides information regarding the distances between images that can be used to facilitate alignment. However using a plenoptic camera (i.e field of light imaging device) to capture images of the eye is complicated by the fact that the eye is itself an optical instrument that includes a lens. In particular, the existence of the lens complicates using a field of light imaging device to image the retinal of an eye.

There remains, therefore, an unmet need for a low cost imaging or analysis system suitable for non-invasive sub-surface imaging or measurement that does not require focusing and that addresses complicating optical issues of an eye. but that.

SUMMARY OF THE INVENTION

The invention meets at least all of the previously set forth unmet needs. The invention teaches a field of light based method and system suitable for non-invasive target analysis, including in vivo analysis. The invention provides a method for using a field of light imaging device to generate a representation of an attribute of a target, where the target contains at least one element that modifies the direction of the path of optical signals.

In an embodiment according to the invention, the following describes the inventive method: effecting multiple relative locations and relative orientations between the target and the field of light imaging device; capturing at least one field of light data sets of the target at each of the multiple relative locations and orientations by means of the field of light imaging device; generating a first set of multiple images of a surface within the target from the field of light data sets wherein each of the images has an associated meta data set related to the paths of the optical signals used to generate the images, using a first estimate of the element that modifies the direction of the path of optical signals in said target; modifying, at least one time, the first estimate of the element that modifies the direction of the path of optical signals in the target, using a figure of merit derived from processing the first set of multiple images; generating at least one second set of multiple images of a surface within the target from the field of light data sets wherein each of the images has a modified associated meta data set related to the paths of the optical signals used to generate at least a second set of multiple images and wherein the second set of multiple images has an improved figure of merit; and outputting said representation of said attribute of said target.

In a preferred embodiment, the target is an eye, and the output displays a selected aspect of the eye, including, as may be selected by the investigator, measurements of key parameters of the target eye. Measurements of key parameters include, to name a few, the focal length of the lens of the eye, the thickness of the lens, the axial length, a distortion profile of the lens, a distortion profile of the anterior chamber, a distortion profile of the retina. In addition, the output can be an image of the retina.

Further, a system according to the invention is comprised of a field of light imaging device; an illuminating module consisting of a plurality of light sources that emit light radiation centered on at least a first and a second wavelength, where said first wavelength does not equal said second wavelength; a partially reflective element or mirror, where the partially reflective mirror is positioned so as to reflect radiation to the target from the illuminating module, and from the target to the field of light imaging device; a display, said display positioned in an optically unobstructed linear relation to the target so that the display is viewable from the position (i.e. from the point of view) of the target; a processing and control module coordinating the position of the target, and coordinating the synchronous output of the illuminating module output with image capture by the field of light imaging device; and an output and storage device. In alternate embodiments, the system may include at least one camera and any number of additional display modules.

In a preferred embodiment, where the target is the eye, the system provides measurements and images of the eye in vivo, especially, for example, measurements and images of the cornea, the lens, lens thickness, lens curvature, axial length, and characteristics of the retina. However, the inventive method and system is not limited to in vivo applications or to an eye.

DETAILED DESCRIPTION OF AN EMBODIMENT THE INVENTION

Figure 1:
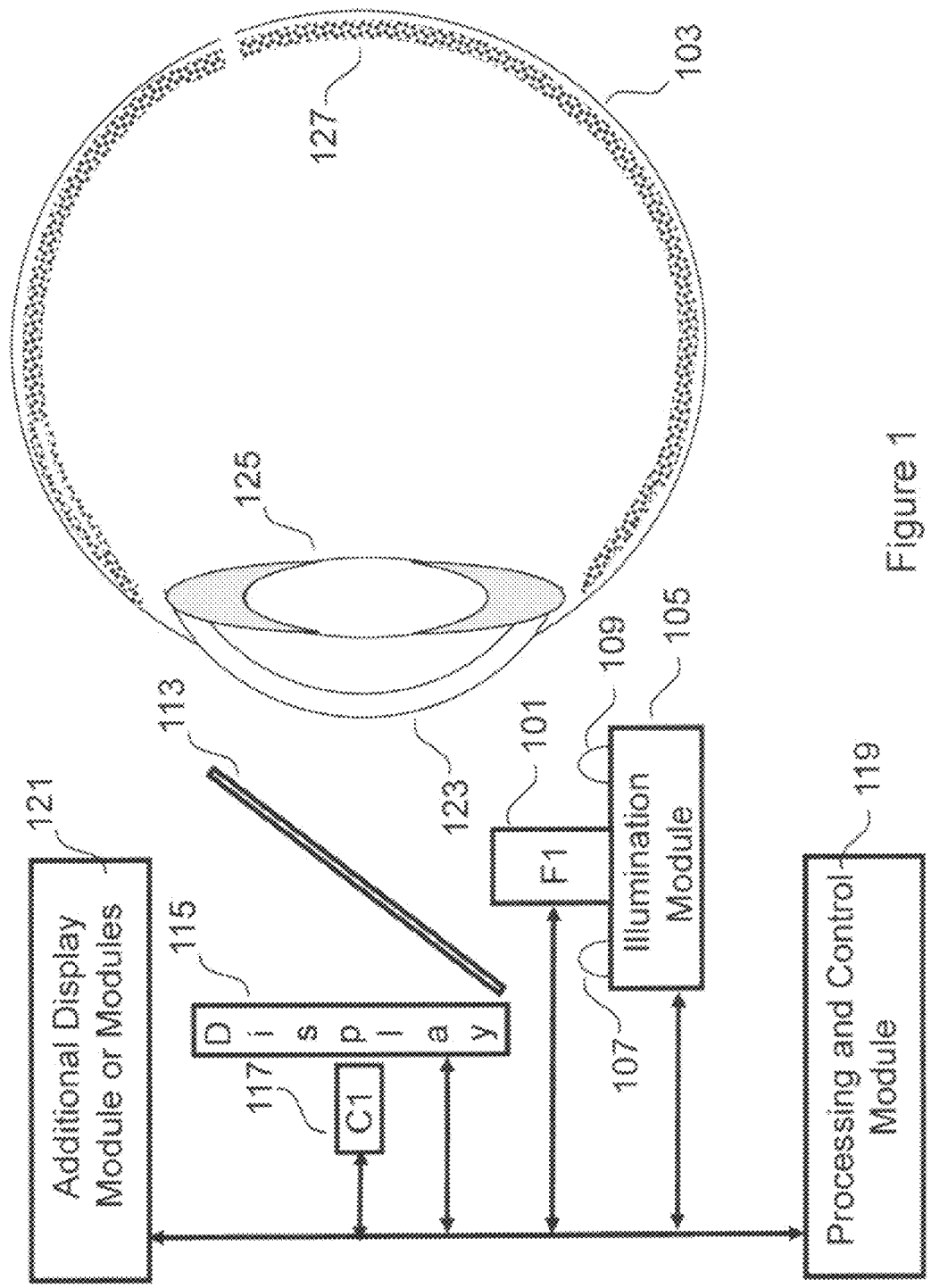
FIG. 1 is an illustration of the overall analysis system according to the invention.

The invention taught herein is an imaging or analysis system suitable for non-invasive sub-surface imaging or measurement with robust alignment. The invention generating a representation of at least one attribute of a target where the target in question contains at least one element that modifies the direction of the paths of at least some optical signals.

An example of such a target is a living eye which contains a lens that focuses light onto the retina of the eye. In an ideal eye, the eye could be well represented by a small number of attributes that include: a cornea curvature; a distance to the lens (anterior chamber thickness); a lens focal length, an eye axial length and a profile and image of the retina.

The profile of an ideal retina is approximately spherical with a well defined depression referred to as the fovea and a second less regular depression at the optic nerve. An image of an ideal retina would contain a clearly visible web due to blood vessels and visible features corresponding to the fovea and the optic nerve.

In an actual eye, a lens may have more than one focal length (resulting in astigmatism) and in any event may not be uniform. Such non-uniformities can lead to distortion of light paths through the lens and are herein referred to as a distortion profile which would be a three dimensional representation of the physical distortion of the lens. Non-uniformities can also occur in a retina and are also herein referred to as a distortion profile.

When a convention camera images a target that contains an element, such as a lens, that modifies the direction of the path of optical signals, it yields an image that is distorted due to this element and does not have additional information to appropriately correct for the distortion.

A digital field of light camera, however, captures a field of light data set that includes light with incoming paths from all directions. In these circumstances, if the nature of the distortion being introduced by the element that modifies the path of optical signals is known, then meta-data that represents the direction of light paths can be modified to correct for the "re-directing" element and a distortion free image can be obtained.

If the nature of the distortion being introduced by the element that modifies the path of optical signals is not accurately known but aspects of the image to be generated are known, then the nature of the distortion being introduced can be estimated and a new image generated. Comparing the new image to the original, to determine if the known aspects of the image have improved or not, provides a mechanism for iteratively refining the nature of the distortion. In this manner both the nature of the distortion becomes better defined and the resulting image becomes less distorted.

In the case of a human eye more than one element can modify the direction of optical signals and thereby degrade an image of an aspect of eye such as the retina. For example, the lens may have multiple focal lengths and a non-uniform distortion profile, the axial length of the eye may not be optimal for the lens.

However eyes, such as human eyes, have a great deal is similar characteristics. Furthermore, with field of a light data set captured by a field of light imaging device, also referred to as a plenoptic camera, it is possible to generate images of the same region of the retina using light that has travelled through different regions of the lens. It is also reasonable to vary the spatial relationship between the eye (the target) and the field of light imaging device, thereby effecting capturing one or more field of light data sets at multiple relative locations and relative orientations between the target and the field of light imaging device.

Multiple relative locations and relative orientations between the target and the field of light imaging device can be effected by causing the eye of subject (the individual whose eye is being analyzed) to move in response to a fixation point or image or by relying on the inevitable involuntary motion of the subject's eye.

The multiple captured field of light data sets can be processed iteratively by assigning an initial estimate to one or more of the parameters of the element or elements that modify the direction of the path of optical signals in the eye. For example initial estimates of the focal length of the lens or the radius of curvature of the cornea or the axial length of the eye could be based on historical (previously acquired) information or could be based on average population values for individuals of similar characteristics. Alternatively initial estimates of parameters could be obtained by processing some captured field of light data sets.

Multiple images of, for example, regions of the retina could be then generated from the field of light data sets where each the meta-data associated with the images is modified to account for element or elements that modifies the direction of the path of optical signals in the eye to yield a second set of images.

The difference in this second set of images with respect to the first images provides a mechanism for assessing whether the quality of images has improved or not. For example the sharpness of aspects of the image, such as blood vessels, may be used as a figure of merit.

The process of modifying the meta-data and assessing a figure merit of the resulting images may be performed iteratively refining the nature of and magnitude of parameters or properties of elements that cause optical distortion. Parameters may be iteratively adjusted in a direction that yielded images with an improved figure of merit. Maximum likelihood techniques may be used to fit parameters to image data.

The results or output of this processing are more accurate values of key optical parameters of the eye, such as lens focal length or lengths, curvature of the cornea, axial length and distortion profiles of surfaces of the eye. Another result or output of this processing is a more accurate or sharper image or set of images of surfaces of the eye and in particular of the retina of the eye. In general the results or output of this processing is a representation of an attribute of the target, which in the preferred embodiment is a living eye.

A preferred embodiment of the invention is illustrated in and described with respect to FIG. 1 of Sheet 1. A field of light imaging device 101 is used to capture multiple images of a target 103, which in the preferred embodiment is a living eye.

The target 103 is illuminated by an illuminating module 105 which consists of multiple light sources, such as light emitting diodes (LEDs), two of which are depicted as 107 and 109 of FIG. 1. In the preferred embodiment LEDs, such as 107 and 109, emit light radiation centered on different wavelengths. The center wavelengths can include, but are not limited to, visible and infra-red wavelengths.

In the preferred embodiment, one or more LEDs of the illuminating module 105 are pulsed to illuminate the target for a short period of time. Such pulsing is synchronous with the field of light imaging device 101 capturing one or more images of the target 103. The duration of light radiation pulses can be short so as not to cause the opening of iris of the eye to reduce. while an embodiment the illuminating module 105 could include a light source centered on one wavelength. Multiple light sources centered on different wavelengths enables enhanced image processing of images of aspects of a target, for example, the retina of an eye.

In the preferred embodiment light radiation is directed to the target 103 from the illuminating module 105 and from the target 103 to the field of light imaging device 101 by a partial reflective mirror 113. The partial mirror 113 can be partially reflective over a broad range of wavelengths or reflective at some selected wavelength ranges and transmissive at other wavelength ranges or may be partially reflective at some wavelength ranges and highly transmissive or reflective at other wavelength ranges. The partially reflective mirror enables an optically un-obstructed linear relation to the target so that a display 115 is viewable from the position of said target and simultaneous illumination of the target by the illuminating module and capture of field of light data sets by the field of light imaging device.

In the preferred embodiment the display 115 is visible to the eye of a subject through the partial reflective mirror 113. Suitable displays include, but are not limited to, conventional liquid crystal display (LCD) or a single LED or an array of LEDs. The display 115 may be used to provide guidance or instructions to the individual whose eye is being measured or monitored. Such guidance or instructions may include displaying a fixation pattern to help determine the orientation or location of the eye.

Other forms of guidance or instructions includes, but is not limited to, displaying readable instructions or displaying stationary or moving pictures that will cause the eye to move in a substantially pre-determined manner. Visual instructions could also be generated in real time, i.e. as live instructions. Guidance and instructions could also be given by an optional audio unit, either in a pre-recorded or live manner. In the case of live instructions, such instructions could be generated locally or remotely.

In some embodiments an optional conventional camera 117 is located either in association with the display 115 or the field of light imaging device 101 to provide additional information to the system regarding the location of the eye. In the case of a camera 117 associated with the display 115, the camera 117 could be behind the display 115 with a small aperture in the display 115 allowing light to reach the lens of the camera 117.

A processing and control module 119 coordinates the positioning of the eye by means of the guidance and instructions display 115 in conjunction with monitoring the location of the eye 103 by the field of light imaging device 101 an the optional camera 117. The processing and control module 119 also coordinates pulsing one or more of the LEDs of the control module 105 and synchronously capturing and storing one or more field of light data sets using the field of light imaging device 101 and the optional camera 117.

Some embodiments could have one or more optional additional display modules which could be either local, remote or both local and remote. In some embodiments the processing and control module 119 would send the acquired field of light data sets to a remote location via the Internet for further processing.

Processing a field of light data sets captured by field of light imaging device 101 includes generating multiple in-focus images derived from the same captured field of light data set to generate clear images of different regions of the eye.

Processing a field of light data sets also includes generating meta-data and processing such meta-data to derive measurements of aspects of the eye, such as the distance between surfaces or the curvature of surfaces.

Processing a field of light data sets also includes applying transformations to ray paths of at least some of the rays within the field of light to account for light rays passing through and being modified by optical components of the eye. Such optical components include, but are not limited to, the lens and the anterior chamber of the eye.

Processing a field of light data set also includes fitting one or more parameters of at least one optical component of the eye to optimize the degree to which a second component of the eye conforms to typical characteristics of the second component of the eye.

For example, the curvature of the cornea 123 could be estimated from the light rays that are emanating from the surface of the cornea, then the parameters that determine the focusing properties of lens 125 of the eye could be estimated from the light rays that are emanating from the retina of the eye.

A field of light data set can be processed to generate in-focus or "sharp" images of aspects of the retina 127, such as blood vessels, assuming some initial estimates of parameters of the eye, such as focal length of the lens and axial length of the eye. The meta-data acquired in generating such sharp images of aspects of the retina may then be used to refine the initial estimates of parameters of the eye.

Multiple field of light data sets taken with the eye in multiple relative locations and orientations can be processed in this manner to determine a maximum likelihood fit of a relatively small number of parameters that determine to a substantial degree the operation of the eye and thereby key parameters of the eye may be determined or in effect measured.

Key measurements of the eye may, for example, be used to determine the appropriate artificial lens to insert as a replacement for an inter-ocular lens that has been degraded by the presence of a cataract.

In addition to yielding measurements of a relatively small number of key parameters, the process of fitting a large number of field of light data sets to an initially somewhat idealized model of the eye also provides a mechanism for determining distortions of key components of the eye, such as the lens or the retina.

Furthermore the ability to determine key parameters and to determine distortions of key components enables generating more clear images of aspects of the eye, such as the retina.

Figure 2:
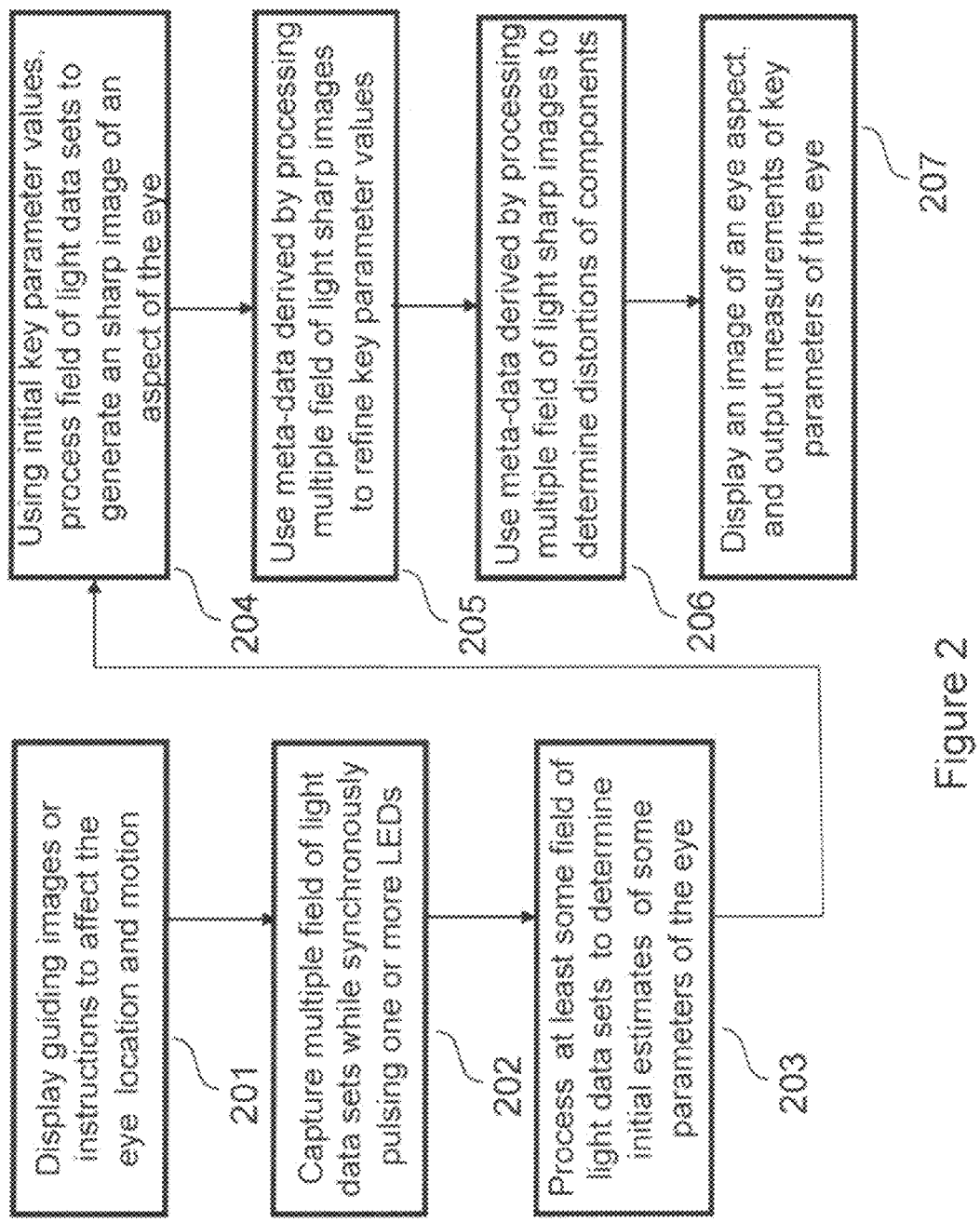
FIG. 2 is an illustration of the steps involved in using the overall analysis system.

The steps taken to determine key parameters, distortions of key components and to generate clear images of aspects of the eye are depicted in FIG. 2.

Step 1: Display guiding images, such as fixation patterns, or readable instructions, such as "turn to the left" or fixed or moving images, so as to affect the eye location and motion.

Step 2: Capture multiple field of light data sets while synchronously pulsing one or more light sources either individually or in combination, where such light sources may be LEDs that emit visible or infra-red radiation.

Step 3: Process at least some field of light data sets to determine initial estimates of some key parameters of the eye, such as the radius of the cornea or the axial length of the eye.

Step 4: Process at least some field of light data sets to generate sharp or in-focus images of some aspects of the eye, such as a sharp or in-focus image of a region of the retina of the eye.

Step 5: Use meta-data derived by such processing of multiple field of light data sets to generate multiple sharp or in-focus images to refine the values of key parameter such as axial length and lens focusing parameters.

Step 6; Use meta-data derived by processing multiple field of light data sets to generate multiple in-focus images to further determine distortions of components of the eye, such as the lens or the retina. Such distortions include, but are not limited to, astigmatic focusing parameters of the lens or distortions of the symmetry or height profile of the fovea region of the retina.

Step 7: Having determined the values of key parameters and the nature and magnitude of the distortions of key components, multiple field of light data sets can be reprocessed in conjunction with the refined key parameter values and the component distortion information to generate enhanced quality images of regions of the eye, such as the retinal region. Aspects of the eye for which enhanced quality images have been generated can be displayed either remotely or locally. Measurements of key parameters of the eye can also be output as numerical values either separately or in conjunction with related images.

Processing to refine key parameters or to determine distortions (which may be stored as maps) can utilize conventional processing techniques including, but not limited to, maximum likelihood techniques. The above steps can also be repeated in an iterative manner to achieve increasingly refined measurements and images. Previously stored results can be used as or to assist with initial values, or can be used to compare with present results to determine the progression or recession of a condition.

While the preferred embodiment described above is directed towards an ophthalmic application, it should be understood that the above description is intended to be illustrative and not restrictive. Other applications could include inspecting optical components or systems for quality control purposes, where at least some of the optical components modify or distort the paths of rays of light. More generally the invention enables performing enhanced measurement and imaging of targets that distort the path of optical signals, where for purposes of this invention, optical signals include the full spectrum of electromagnetic radiation.

It can also be appreciated many of the features have functional equivalents that are intended to be included in the invention as being taught. Many variations and combinations of the above embodiments are possible. Therefore the scope of this invention should not be determined with reference to the above description, but instead should be determined with reference to the appended claims and drawings, along with the full scope of equivalents to which such claims and drawings are entitled.

What is claimed is:

1. A method of generating, by means of a field of light imaging device, a representation of an attribute of a target, said target containing at least one element that modifies the direction of the path of optical signals, said method comprising:
   effecting multiple relative locations and relative orientations between said target and said field of light imaging device;
   capturing at least one field of light data sets of said target at each of said multiple relative locations and orientations by means of said field of light imaging device;
   generating a first set of multiple images of a surface within the target from said field of light data sets wherein each of said images has an associated meta data set related to the paths of the optical signals used to generate said images, using a first estimate of said element that modifies the direction of the path of optical signals in said target;
   modifying, at least one time, said first estimate of said element that modifies the direction of the path of optical signals in said target, using a figure of merit derived from processing said first set of multiple images;
   generating at least one second set of multiple images of a surface within the target from said field of light data sets wherein each of said images has a modified associated meta data set related to the paths of the optical signals used to generate at least a second set of multiple images and wherein said second set of multiple images has an improved figure of merit and
   outputting said representation of said attribute of said target.

2. A system for analyzing a target, said system comprising:
   a field of light imaging device;
   an illuminating module, said illuminating module consisting of a plurality of light sources, said light sources emitting light radiation centered on at least a first and a second wavelength, where said first wavelength does not equal said second wavelength;
   a mirror, said mirror partially reflective, and positioned so as to reflect radiation to said target from said illuminating module, and from said target to said field of light imaging device;
   a display, said display positioned in an optically unobstructed linear relation to said target so that said display is viewable from the position of said target;
   a processing and control module, said processing and control module coordinating the position of said target, and coordinating synchronous output of said illuminating module output with image capture by said field of light imaging device; and output and storage device.

3. A system as in claim 2 further including at least one camera, said camera controlled by said processing and control module, and acquiring images of said target.

4. A system as in claim 2 further including at least a second display device.

5. A system as in claim 2 where said illuminating module includes at least two Light Emitting Diodes (LEDs), such that said pulses of emitted radiation are synchronous with said field of light imaging device image capture, and further where said pulse duration is sufficiently short so as to minimize light-exposure-related changes in said target.

6. A system as in claim 2 where said partially reflective mirror enables an optically un-obstructed linear relation to said target so that said display is viewable from the position of said target and simultaneous illumination of the target by said illuminating module and capture of field of light data sets by said field of light imaging device.

* * * * *